United States Patent [19]
Arndt et al.

[11] Patent Number: 4,713,490
[45] Date of Patent: Dec. 15, 1987

[54] PROCESS FOR THE PREPARATION OF ALKYLTHIOACETAMIDINES

[75] Inventors: Michael Arndt, Wuppertal; Hans P. Sehnem, Schwelm, both of Fed. Rep. of Germany

[73] Assignee: Bayer Aktiengesellschaft, Leverkusen, Fed. Rep. of Germany

[21] Appl. No.: 802,799

[22] Filed: Nov. 27, 1985

[30] Foreign Application Priority Data

Dec. 6, 1984 [DE] Fed. Rep. of Germany ....... 3444494

[51] Int. Cl.$^4$ ........................................... C07C 123/00
[52] U.S. Cl. ................................................... 564/225
[58] Field of Search ......................................... 564/225

[56] References Cited
U.S. PATENT DOCUMENTS

| 2,147,400 | 2/1939 | Clark | 568/70 |
| 2,252,723 | 8/1941 | Miescher et al. | 548/353 |
| 3,728,389 | 4/1973 | Hodson et al. | 564/247 |
| 3,896,125 | 7/1975 | Helmo et al. | 562/225 |
| 4,323,571 | 4/1982 | Maurer et al. | 514/269 |

OTHER PUBLICATIONS

Degering, Ed. F. *An Outline of Organic Nitrogen Compounds,* (1950), Univ. Lithoprinters, Ypsilanti, Mich., Publ. at p. 506.
Kirk-Othmer, *Encyclopedia of Chemical Technology,* 2nd Ed., (1970), vol. 20, at p. 211.
Conant, James Bryant et al., *The Chemistry of Organic Compounds,* 45h Ed., (1954), MacMillan Co., Publ. pp. 335-338.
Quayle, Osborne R., *J. Am. Chem. Society.,* (1942), vol. 64, pp. 226-230.

*Primary Examiner*—James H. Reamer
*Attorney, Agent, or Firm*—Sprung Horn Kramer & Woods

[57] ABSTRACT

A process for the preparation of alkylthioacetamidines by the reaction of chloroacetonitrile with ammonium halide in the presence of a catalyst followed by reaction of the resultant chloroacetamidine with an alkyl mercaptan in the presence of an acid acceptor.

10 Claims, No Drawings

PROCESS FOR THE PREPARATION OF ALKYLTHIOACETAMIDINES

The invention relates to a new process for the preparation of alkylthioacetamidines from chloroacetonitrile and alkyl mercaptans in the presence of an alcoholic solution of an alcoholate.

It is already known that alkoxyalkyl derivatives can be prepared by reacting alcoholates with halogenoalkyl derivatives (see, for example, "Methoden der organischen Chemie" ["Methods of organic chemistry"], volume VI/3, page 26, Houben-Weyl-Müller, Thieme-Verlag Stuttgart). It is also known that alkylthioalkyl derivatives can be prepared from the corresponding alkyl mercaptans and halogenoalkyl derivatives (see, for example, "Methoden der organischen Chemie" ["Methods of organic chemistry"], volume IX, page 103, Houben-Weyl-Müller, Thieme-Verlag Stuttgart).

It has now been found that alkylthioacetamidines of the formula (I)

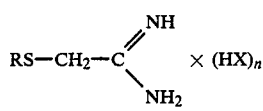 (I)

in which
R represents alkyl,
X represents halogen and
n represents 0 or 1
are obtained if
(a) chloroacetonitrile of the formula (II)

ClCH$_2$CN (II)

is reacted with ammonium halides of the formula (III)

NH$_4$X (III)

in which X has the meaning indicated above, in the presence of catalysts and in the presence of diluents at temperatures between −20° C. and +30° C., to give the chloroacetamidines of the formula (IV)

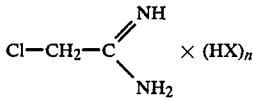 (IV)

in which X and n have the meanings indicated above, and
(b) these compounds of the formula (IV) are reacted, if desired without being isolated, with alkyl mercaptans of the formula (V)

RSH (V)

in which R has the meaning indicated above, in the presence of acid acceptors and in the presence of diluents at temperatures between −20° C. and +30° C. under and a pressure between 1 and 10 bar to give the compounds of the formula (I).

By means of the process according to the invention, it is possible, surprisingly, to carry out the reaction within short reaction times and in high yields, although, according to the state of the art, it would have been necessary to expect the formation of alkoxyacetamidines to a considerable extent. It is an advantageous feature in this process that pollution of the exit air with alkyl mercaptans is largely avoided by the use of closed reactors.

The reaction leading to the preparation of the compounds of the formula (I) is preferably carried out without isolating the intermediate stage (IV).

It is preferable to prepare, by means of the process according to the invention, compounds of the formula (I) in which
R represents alkyl having 1 to 6 carbon atoms,
X represents chlorine or bromine and
n represents 0 or 1.

It is particularly preferable to prepare, by means of the process according to the invention, compounds of the formula (I) in which
R represents methyl, ethyl, n-propyl, i-propyl, n-butyl, i-butyl, sec.-butyl and tert.-butyl,
X represents chlorine and
n represents 0 or 1.

If chloroacetonitrile, ammonium chloride and methyl mercaptan are used as the starting materials for the process according to the invention, the reaction can be represented by the following equation:

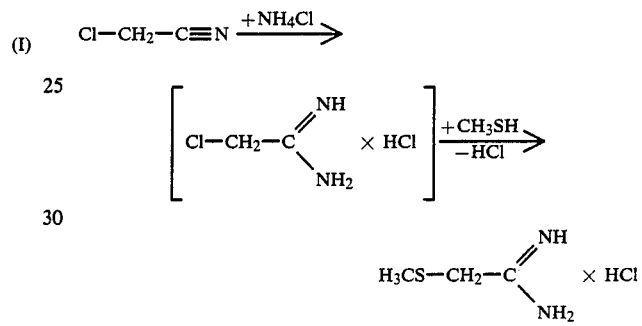

The compound of the formula (II), which is required as the starting material for carrying out the process according to the invention, is a compound generally known in organic chemistry.

The further compounds required as starting materials for the process according to the invention are defined in a general manner by the formulae (III), (IV) and (V). In these formulae, X and n and R represent the radicals which have been mentioned above in the definition of the compounds of the formula (I).

The following may be mentioned as examples of the compounds of the formula (III): ammonium chloride, bromide and iodide.

The following may be mentioned as examples of the compounds of the formula (IV): chloroacetamidine, chloroacetamidine hydrochloride and chloroacetamidine hydrobromide.

The following may be mentioned as examples of the compounds of the formula (V): methyl, ethyl, n-propyl, i-propyl, n-butyl, i-butyl, sec.-butyl and tert.-butyl mercaptan.

The compounds of the formulae (III), (IV) and (V) are compounds generally known in organic chemistry.

The process according to the invention is carried out in both reaction stages in the presence of diluents. Suitable diluents under the conditions of the reaction are inert solvents. These include, in particular, alcohols, such as methanol, ethanol and n-propanol. It is preferable to employ methanol as the solvent.

The process according to the invention is carried out in stage (a) in the presence of catalysts. The following catalysts are preferentially suitable: alkali metal alcoholates, such as sodium methylate or ethylate and potassium methylate or ethylate. It is preferable to employ sodium methylate or ethylate as the catalyst.

The process according to the invention is carried out in stage (b) in the presence of acid acceptors. Acid acceptors which are preferentially suitable are the alkali metal alcoholates mentioned above. It is preferable to employ sodium methylate or ethylate as the acid acceptor. The diluent employed is methanol if sodium methylate is employed, and is ethanol if sodium ethylate is employed.

The process according to the invention is carried out in both stages in general at temperatures between −20° C. and +30° C., preferably between −10° C. and +20° C. The reactions are preferably carried out in an inert gas atmosphere. Argon or nitrogen is preferentially suitable as the inert gas. The reaction is preferably carried out in the presence of nitrogen.

The process according to the invention is preferably carried out under normal pressure in stage (a). Stage (b) is generally carried out under a pressure between 1 and 10 bar, preferably between 1 and 5 bar.

In carrying out the process according to the invention, 0.01 to 0.2 mole, preferably 0.05 to 0.15 mol, more preferably 0.01 to 0.1 mole of catalyst and 1 to 2.00 moles, preferably 1 to 1.5 moles, of ammonium halide of the formula (III) are employed in stage (a) for 1 mole of chloroacetonitrile of the formula (II). 1 mole of acid acceptor and 1 mole of alkyl mercaptan of the formula (V) are added to the reaction mixture for the further reaction corresponding to stage (b).

The reaction product of the formula (I) can be worked up by customary methods. It is preferable to employ the reaction product in the next reaction without further working up, if desired after filtering off the inorganic salts.

The compounds of the formula (I) which can be prepared by the process according to the invention are important intermediate products for the synthesis of insecticides. Thus, for example, the substituted N,N-dimethyl-0-pyrimidinylcarbamic acid esters, compounds having a high insecticidal potency, can be prepared from them (see, for example, German Offenlegungsschrift No. 2,928,185).

The further processing of the compounds of the formula (I) to give known pest-combating agents may be illustrated using the following equation as an example:

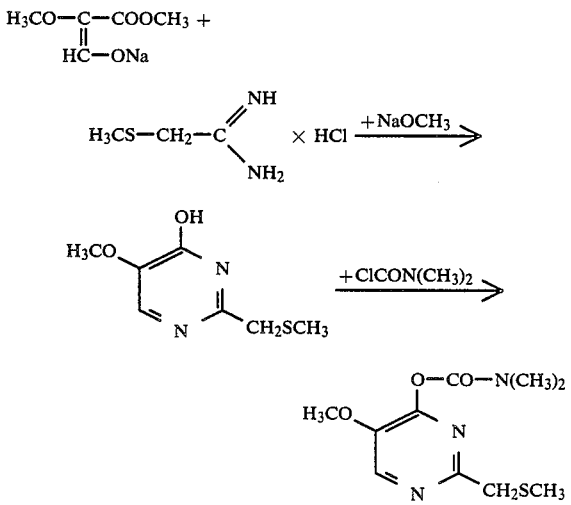

PREPARATION EXAMPLE

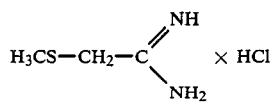

113 kg(1496 moles)of chloroacetonitrile are added a 0° C. to 5° C. to a mixture of 100 kg (3125 moles) of methanol and 4 kg (74 moles) of sodium methylate. The mixture is stirred for a further 30 minutes at 0° C. to 5° C. and 87.5 kg (b 1636 moles) of ammonium chloride are then added at 0° C. to 5° C. The mixture is again stirred for a further 30 minutes at the same temperature, 316 kg of 25% strength methanolic sodium methylate solution are added and 76 kg (1575 moles) of methyl mercaptan are then injected into the closed reactor. The reaction mixture is stirred for a further 30 minutes at 0° C. to 5° C. and solids are removed by filtration. The whole reaction is carried out under an atmosphere of nitrogen. Methanol is removed from the filtrate by distillation, and the reaction product is recrystallised from acetone.

190 kg (90% of theory) of 2-methylthioacetamidine hydrochloride of melting point 70° C. are obtained in this way.

We claim:
1. A process for the preparation of an alkylothioacetamidine of the formula

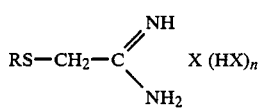

in which
R represents alkyl,
X represents halogen and
n represents 0 or 1,
wherein
(a) a chloroacetonitrile of the formula

is reacted with an ammonium halide of the formula

in which
X has the meaning indicated above, in the presence of an alkali metal alcoholate and in the presence of an alcohol at a temperature between −20° C. and ±30° C., to give a chloroacetamidine of the formula

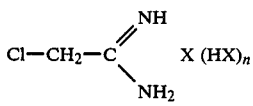

in which
X and n have the meaning indicated above, and
(b) the cholroacetamidine is then reacted, if desired without being isolated, with an alkyl mercaptan of the formula

in which
R has the meaning indicated above, in the presence of an acid acceptor and in the presence of an alcohol at a temperature of between −20° C. and ±30° C. and under a pressure between 1 and 10 bar, to give an alkylthioacetamidine wherein 0.01 to 0.2 mole of alkali metal alcoholate and 1 to 2.00 moles of ammonium halide are employed in stage (a) for 1 mole of chloroacetonitrile and 1 mole of acid acceptor and 1 mole of alkyl mercaptan are added in stage (b).

2. A process according to claim 1, wherein the chloroacetamidine is not isolated.

3. A process according to claim 1, wherein an alkylthioacetamidine
wherein
R is $C_1$-$C_6$-alkyl,
X is chlorine or bromine and
n is 0 or 1
is prepared.

4. A process according to claim 1, wherein an alkylthioacetamidine
wherein
R is methyl, ethyl, n-propyl, i-propyl, n-butyl, i-butyl, sec.-butyl or tert.-butyl,
X is chlorine and
n is 0 or 1
is prepared.

5. A process according to claim 1, wherein methylthioacetamidine hydrochloride is prepared.

6. A process according to claim 1, wherein an alkali metal alcoholate is employed as the acid acceptor in stage (b).

7. A process according to claim 1, wherein the reaction is carried out at a temperature of between −10° C. and +20° C. in both of the stages (a) and (b).

8. A process for the preparation of an alkylthioacetamidine of the formula

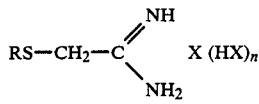

in which
R represents alkyl,
x represents halogen and
n represents 0 or 1
wherein a chloroacetamidine of the formula

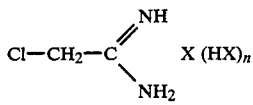

in which
X and n have the meanings indicated above, is reacted with an alkyl mercaptan of the formula

R—SH in which
R has the meaning indicated above, in the presence of an acid acceptor and in the presence of an alcohol at a temperature of between −20° C. and +30° C. and under pressure between 1 and 10 bar.

9. A process according to claim 1 wherein 0.01 to 0.1 mole of alkali metal alcoholate and 1 to 2.00 moles of ammonium halide are employed in stage (a) for 1 mole of chloroacetonitrile and 1 mole of acid acceptor and 1 mole of alkyl mercaptan are added in stage (b).

10. A process according to claim 1 wherein 0.05 to 0.15 mole of alkalimetal alcoholate and 1 to 1.5 moles of amminium halide are employed in stage (a).

* * * * *